(12) United States Patent
Saville et al.

(10) Patent No.: US 7,892,805 B2
(45) Date of Patent: Feb. 22, 2011

(54) METHOD OF ENHANCING ENZYME ACTIVITY AND ENZYME SOLUTION HAVING ENHANCED ACTIVITY

(75) Inventors: Bradley A. Saville, Toronto (CA); Mikhail I. Khavkine, Newmarket (CA)

(73) Assignee: Immortazyme Company, Oakville, Ontario (CA)

( * ) Notice: Subject to any disclaimer, the term of this patent is extended or adjusted under 35 U.S.C. 154(b) by 269 days.

(21) Appl. No.: 10/797,019

(22) Filed: Mar. 11, 2004
(Under 37 CFR 1.47)

(65) Prior Publication Data
US 2004/0259219 A1    Dec. 23, 2004

(30) Foreign Application Priority Data
Mar. 13, 2003    (CA)    .................................... 2421832

(51) Int. Cl.
*C12N 9/26* (2006.01)
(52) U.S. Cl. ........................ 435/201; 435/176; 435/181; 435/188
(58) Field of Classification Search ................. 435/183, 435/201
See application file for complete search history.

(56) References Cited

U.S. PATENT DOCUMENTS

| | | | |
|---|---|---|---|
| 4,204,041 A * | 5/1980 | Bailey et al. ................. | 435/177 |
| 6,582,606 B2 | 6/2003 | Lausten et al. | |
| 2002/0020668 A1 | 2/2002 | Lausten et al. | |

FOREIGN PATENT DOCUMENTS

| | | |
|---|---|---|
| GB | 1 082 370 | 9/1967 |
| GB | 1091347 | 11/1967 |
| GB | 1 507 792 | 4/1978 |
| JP | 560003631 | 1/1981 |
| JP | 560003632 | 1/1981 |
| JP | 60092433 | 5/1985 |
| RO | 90071 | 8/1986 |

OTHER PUBLICATIONS

Schuster et al., The effect of charcoal treatment on microsomal Cytochrome P-450, FEBS letters, vol. 74, Feb. 1977, p. 107-110.*
Aikat et al, Biotechnology Letters, vol. 23, 2001, p. 295-301.*
Bailey et al, Biotechnology adn Bioengineering, vol. 25, 1983, p. 1923-1935.*
http://www.usm.maine.edu/~rhodes/biochemLab/text/HdtPurLys/HDTPurLys03.html, Oct. 8, 2002.*
http://www.ap-lab.com/circular_dichroism.htm, Jul. 6, 2006.*
Shenoy et al , Journal of Bioscience vol. 7, Jun. 1985 p. 399-419.*
"Activated Carbon," National Organic Standards Board Technical Advisory Panel Review Compiled by OMRI for the USDA National Organic Program, Aug. 14, 2002, pp. 1-23.
Milcent, et. al., "Clarification of Lactic Acid Fermentation Broths," Separation and Purification Technology, 22-23 (2001) pp. 393-401.

Tsun, et. al., "Recovery and Purification of Thuringiensin from the Fermentation Broth of *Bacillus thruingiensis*," Bioseparation 7: pp. 309-316 (1999).
Office Action mailed Jul. 29, 2008 in corresponding European Patent Patent Application No. 04718893.3.
Liljedahl, "Evaluation of Chromatagraphic Media for Membrane Protein Purification," MSc. Thesis, Uppsala University School of Engineering, 2001, pp. 1-20.
Kerkhoff et al., "Solubilization, Partial Purification and Photolabeling of the Integral Membrane Protein Lysophospholipid:acyl-CoA Acyltransferase (LAT)," Eur. J. Biochem, 267, 6339-6345 (2000).
Cornell lab manual for BIOBM330. http://instruct1.cit.cornell.edu/Courses/biobm330/protlab/Strategy.html, obtained from internet May 1, 2007.
Instructional materials for the MATC Biotechnology program in Madison, WI http://matcmadison.edu/biotech/resources/proteins/labManual/chapter_1.htm, obtained from internet May 1, 2007.
Wingfield et al., Purification and characterization of a methionine-specific aminopeptidase from *Salmonella typhimurium*, Eur. J Biochem. 180.23-32 (1989).
MacKay et al., "Identification and Isolation of a 155-KDa Protein with Neuropathy Target Esterase Activity," Fundamental and Applied Toxicology, vol. 30, pp. 23-30, (1996).
Pimenov et al., "The Adsorption and Deactivation of Microorganisms by Activated Carbon Fiber," Separation Science and Technology 36(15), 3385-3394, (2001).
Hydamaka et al., "Control of Color Problems During Recycling of Food Process Waters," Food Science Department at the University of Manitoba, pp. 237-256, Dec. 1976 Environmental Protection Technology Series v. 600/2-76-304.
Kelly, et. al., "The Use of Circular Dichroism in the Investigation of Protein Structure and Function," Curr. Protein and Peptide Sci., 1, 349-384, (2000).
Lendenmen, et. al., "2-Aminophenol 1,6-Dioxygenase: a Novel Aromatic Ring Cleavage Enzyme Purified from *Pseudomonas pseudoalcaligenes* JS45," J. Bacteriol., pp. 6227-6232, (1996).
Chen et al., "D-Ribulose-5-Phosphate 3-Epimerase: Cloning and Heterologous Expression of the Spinach Gene, and Purification and Characterization of the Recombinant Enzyme," Plant Physiol. 118: 199-207, (1998).

(Continued)

*Primary Examiner*—Ralph Gitomer
*Assistant Examiner*—Tiffany M Gough
(74) *Attorney, Agent, or Firm*—Jeffrey S. Melcher; Manelli Denison & Selter PLLC

(57) ABSTRACT

A method of enhancing the intrinsic activity of an enzyme in a raw enzyme solution, the method comprising treating the raw enzyme solution with an effective amount of a purifying agent, most preferably, activated carbon, to effect the enhancement and provide an enzyme solution of enhanced activity. Preferred enzymes are amylase, glucoamylase, cellulase, xylanase, and all other group 3 hydrolases.

40 Claims, 5 Drawing Sheets

OTHER PUBLICATIONS

Walsh, "Proteins: Biochemistry and Biotechnology," Wiley, West Sussex, England. pp. 156-161 (2002).

Sadana, "Bioseparation of Proteins," Academic Press, San Diego, pp. 1-15, 135, 136, 178, 187, and 245 (1998).

Ladisch, et. al., "Protein Purification: From Molecular Mechanisms to Large Scale Processes," ACS Symposium Series 427 (1990).

Bailon, et. al., "Recovery of Recombinant Proteins by Immunoaffinity Chromatography", pp. 150-167, 1990.

Harrison, "Protein Purification Process Engineering," Marcel Dekker, New York, pp. 6, 7, 44, 45, 52, 53, 128-131, 136, 137, 146, 147, 152-155, 172-175, 210 and 211(1994).

Stein, "Fundamentals of Protein Biotechnology," Marcel Dekker, New York, pp. 145, 161, and 162 (1990).

Wheelwright, "Protein Purification: Design and Scale up of Downstream Processing," Hanser Publishers, Munich, pp. 32, 33, 62, 63, 80, 82, 172, and 186 (1991).

Davis, "Covalent immobilisation of laccase on activated carbon for phenolic effluent treatment", Appl Microbiol Biotechnol (1992) 37:474-479.

Sotiropoulou, et. al, "Lowering the detection limit of the acetylcholinesterase biosensor using a nanoporous carbon matrix", Analytica Chimica Acta 530 (2005) 199-204.

Kibarer, et. al., "Optimization studies on the features of an activated charcoal-supported urease system, Biomaterials". vol. 17, No. 15, pp. 1473-1479. (1996).

Roth, et. al., β-Galactosidases (*Escherichia coli*) with Double Substitutions Show That Tyr-503 Acts Independently of Glu-461 but Cooperatively with Glu-537, Journal of Protein Chemistry, vol. 22, Nos. 7/8, Nov. 2003.

Majunath, et. al., "Fungal glucoamylases," J. Appl. Biochem., vol. 5, pp. 235-260 (1983.

International Search Report for PCT/CA2004/000370, Jul. 2, 2004.

Bgibeaut, David M, "Synthesis of (1-3), (1-4)-Beta-D-Glucan in the Golgi Apparatus of Maize Ceoleoptiles," Proceedings of the National Academy of Sciences of the U.S., vol. 90, No. 9, 1993, pp. 3850-3854.

Schuster, I, "The Effect of Charcoal Treatment on Microsomal Cytochrome P-450," FEBS Letters, vol. 74, No. 1, 1977, pp. 107-110.

Rani, A, "Preparation and Characterization of Amyloglucosidase Adsorbed on Activated Charcoal," Journal of Molecular Catalysis B Enzymatic, vol. 10, No. 5, Oct. 2000, pp. 471-476.

Cho, Y, "Immobilization of Enzymes on Activated Carbon Properties of Immobilized Gluco Amylase EC-3.2.1.3 Glucose Oxidase EC-1.1.3.4 and Glucono Lactonase," Biotecnology and Bioengineering, vol. 20, No. 10, 1978, pp. 1651-1665.

\* cited by examiner

METHOD OF ENHANCING ENZYME ACTIVITY AND ENZYME SOLUTION HAVING ENHANCED ACTIVITY

FIELD OF THE INVENTION

This invention relates to the use of enzymes for industrial processes, particularly, purification methods advantageous for the enhancement of enzyme activity and stability.

BACKGROUND OF THE INVENTION

The industrial use of enzymes is often limited by their high cost and rapid inactivation. Soluble enzymes are lost with the product at the conclusion of a process, and must be replenished. One area of technological development involves modification of proteins to enhance their activity and/or stability. Processes, such as those involving site-directed mutagenesis and the cultivation of wild forms of enzymes in extreme environments, i.e. extremophiles, have led to significant advances in enzyme technology involving the reduction in the cost per unit of enzyme activity.

Another means to improve the economic feasibility of enzymes for industrial processes is through enzyme immobilization onto a matrix, which may facilitate re-use of the enzyme. Immobilization research has focused upon means to enhance the transfer of enzymes onto the support, and upon means to ensure that the immobilized enzymes remain active. Inactivation of enzymes during catalytic turnover is, however, a key obstacle which may limit the economic feasibility of enzyme-mediated processes. Enzymes may be inactivated by extremes of temperature, pH, shear, and also by free radicals and other reactive species present in the reaction medium. Immobilization technology has the potential to reduce such enzyme inactivation, and, thus, extend the useful lifespan of the enzymes.

Activated carbon is a well-known absorbent and has been previously used for enzyme immobilization via absorption (A. S. Rani, M. L. M. Das, S. Satyanarayana, J. Mol. Catal. B. Enzymatic, 10, 471, 2000), or following derivatization or cross-linking. It is also frequently used for purification of water, beverages, and other process streams. Activated carbon has been used to remove phenolics and phenolic exudates from cultures of *A. Canadensis*, to facilitate cell growth (G. M. Roy, Activated Carbon Applications in the Food and Pharmaceutical Industries, Technomic Publishing Co., Lancaster, Pa., 1995). It has also been used for removal of amino acids from protein hydrolysate solutions (Roy, ibid), and for removal of phenolics from soy protein extracts. Activated carbon has also been used to remove chill-sensitive proteins from beer (J. W. Hassler, Purification With Activated Carbon, Chemical Publishing Co., New York, 1974). U.S. Pat. No. 6,582,606 discusses the benefits of activated carbon for microfiltration, in order to reduce fouling of ultrafiltration membranes and enhance separation. However, the prior art is silent as to the effect of activated carbon in enhancing the activity of enzyme solutions.

SUMMARY OF THE INVENTION

It is the object of the present invention to produce an enzyme form of enhanced activity for use in industrial processes which improved enzyme form is produced by reagent purification.

Accordingly, in one aspect the invention provides a method of enhancing the intrinsic activity of an enzyme from a raw enzyme solution, said method comprising treating said enzyme solution with an effective amount of a purifying agent for a sufficient period of time, preferably, activated carbon to effect said enhancement and provide an enzyme solution of enhanced activity.

The raw enzyme solution comprises one or more proteins resulting from a fermentation process.

Thus, the invention, as hereinabove defined, results from the surprising discovery that purification of a raw enzyme solution using the purifying agent, most preferably, activated carbon, can dramatically enhance the activity of the enzyme solution.

By the term "raw enzyme solution" in this specification is meant a commercial grade formulation, produced by fermentation from any one of a variety of bacterial and microbial sources. In the case of an extracellular enzyme, the crude enzyme extract is obtained by, e.g., filtration or centrifugation of the fermentation broth, thus isolating the enzyme from protein debris. If the enzyme is produced intracellularly, the cells are lysed prior to filtration/centrifugation. The crude enzyme extract may also be subjected to membrane separation, ion exchange, or ultrafiltration to produce a partially purified, concentrated enzyme extract rich in the desired enzyme, and relatively devoid of other competing/contaminating enzymes and/or cells. The enzyme solution may also include residual components from the fermentation medium, protease inhibitors, and stabilizing agents.

We have found that the specific enzyme activities, particularly of commercial enzyme formulations are greatly enhanced after purification with, for example, activated carbon.

We have found that the purified enzymes exhibit a significant change in UV-VIS and Far UV (CD) spectra, exhibit substantially different properties as demonstrated by gel electrophoresis and by chromatographic separation, and have increased enzyme activity. Without being bound by theory, we believe that this positive effect of activated carbon purification is a result of improved enzyme substrate interactions, interconversion between inactive and active forms of the protein (enzyme), or the removal of inhibitors. Commercial enzyme preparations, formulations and the like, are, generally, colloid solutions that may have a significant amount of dispersed solids, such as, cell debris that may adsorb onto the enzyme and shield the enzyme active centre, and, thus, limit access to bulky substrates, such as starches. Accordingly, enzyme active centre shielding by dispersed solids may, thus, decrease the enzyme specific activity.

In a further aspect, the invention provides a method as hereinabove defined wherein said enzyme solution of enhanced activity shows in the CD spectral range of 205-230 nm; a relative absorbance intensity lower than said raw enzyme solution.

Preferably, the ratio of A to B the ratio of A' to B', wherein A is the amount of enzyme in the enzyme solution of enhanced activity; B is the a mount of said organic entities A' is the amount of enzyme and B' the amount of said organic entities in said raw enzyme solution.

By the term "raw enzyme in connection with its weight" as used in this specification and claims is meant the volume of the raw enzyme solution x the density of the raw enzyme solution.

The weight ratio of raw enzyme to purifying agent is dependent on the enzyme and purifying agent. Preferably, the ratio is not greater than 50:1, more preferably, not greater than 25:1, and still more preferably not greater than 15:1. A preferred ratio for use with activated carbon as the purifying agent provides 11 g raw enzyme purified with 0.75 g activated carbon.

Accordingly, the invention provides in a preferred aspect, a method as hereinabove defined wherein said ratio is not greater than 50, preferably, the ratio is not greater than 25, and more preferably, not greater than 15.

Typical contact, i.e. residue time, of the raw enzyme with the purifying agent may be selected by the skilled person, but could be as short as less than 15 minutes, preferably 30 minutes, and more preferably at least 1-2 hours, depending on the enzyme and the purifying agent.

Preferably, the enzyme is selected from the group consisting of amylase, glucoamylase, cellulase, xylanase and any other group 3 hydrolase.

The resultant enzyme solution of enhanced activity may be used in admixture with the activated carbon, in its intended subsequent industrial process, such as, the hydrolysis of corn starch, if desired.

Most preferably, the activated carbon is removed, preferably, by filtration or centrifugation, prior to subsequent use of the enhanced activity formulation, which filtration method comprising passing said enzyme solution through a column containing an effective amount of said purifying agent.

We have discovered that the raw enzyme solution obtained as a product of a commercial, fermentation-derived product is preferably diluted with water prior to or at the time of admixture, with the purifying agent by a factor of at least three, and more preferably by about 5-10 times, in the process according to the invention. The raw enzyme solution is diluted with a desired amount of water or aqueous buffer solution for ease of mixing and separation of the activated carbon while, most surprisingly, at least maintaining its original level of enzymatic activity. Thus, the process according to the invention comprising the dilution of the raw enzyme solution provides a more efficacious use of the enzyme.

In a further aspect, the invention provides an enzyme aqueous formulation of enhanced activity when made by a process as hereinabove defined when suitably diluted with water.

In a further aspect, the invention provides a method of treating a substrate susceptible to enzymatic reaction with an enzyme, said method comprising treating said substrate with an enzyme formulation of enhanced activity as hereinabove defined.

The invention is of particular value in the treatment of polysaccharide products such as, for example, starch from, for example, wheat, potatoes and rice, with alpha-amylase, glucoamylase, cellulase, xylanase, glucose isomerase, or any other group 3 hydrolase.

BRIEF DESCRIPTION OF THE DRAWINGS

In order that the invention may be better understood, preferred embodiments will now be described by way of example only, wherein.

DETAILED DESCRIPTION OF PREFERRED EMBODIMENTS

The following examples illustrate the method according to the invention.

EXAMPLE 1

Purification of Alpha Amylase with Activated Carbon

Figure 1:
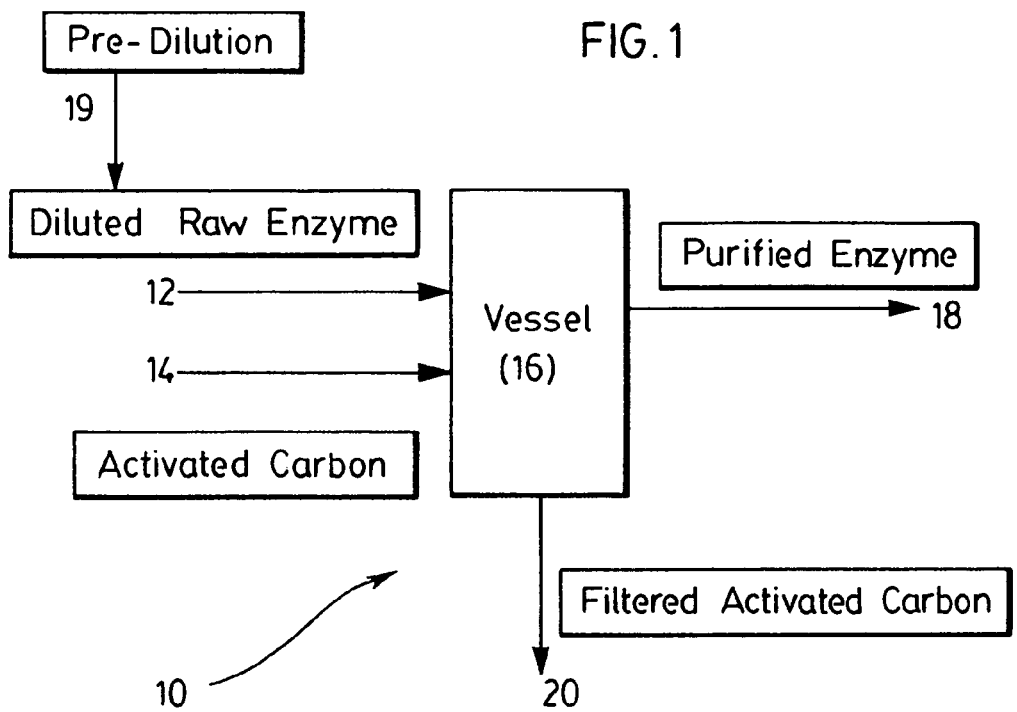
FIG. 1 is a schematic process diagram illustrating a process according to the invention.

A purified enzyme solution was prepared as shown generally as 10 in FIG. 1.

A diluted raw enzyme solution (12), comprising 60 mL raw amylase (Allzyme®, amylase from Alltech) and 270 mL of 0.05M phosphate buffer (pH 6), was prepared and mixed with 24 g of activated carbon (14) for 3 h with magnetic stirring at 300 rpm in a vessel (16). The purified enzyme (18) was separated from the activated carbon (20) by filtration. Assays of the raw enzyme solution, before dilution (12) and the purified enzyme solution (18) were conducted. The activity of the amylase solution (19) before dilution to produce solution (12) was 2035 U/mL, whereas the activity of the purified enzyme (18) was 2010 U/mL, notwithstanding that, due to dilution, the purified preparation contained only about 18 mL of amylase per 100 mL of solution (18). Thus, the activity of the purified enzyme (18), expressed per mL of raw amylase, would be about 11000 U/mL, or about 5.4 times the activity of the original amylase formulation (12). The activity of the diluted enzyme before purification (12) was statistically equivalent to that of the raw enzyme (19), when expressed per mL of raw amylase in the solution.

EXAMPLE 2

Purification of Alpha Amylase with Activated Carbon

An alternative purified enzyme solution (18) was prepared according to FIG. 1 wherein a diluted raw enzyme solution (12), comprising 40 mL raw amylase (Spezyme® Fred amylase, from Genencor) and 360 mL of water was prepared and mixed with 8 g of activated carbon (14) for 12 h with magnetic stirring at 250 rpm in vessel (16). The purified enzyme (18) was separated from the activated carbon (20) by filtration. Assays of the raw enzyme solution before dilution (19) and the purified enzyme solution (18) were conducted. The activity of the amylase solution before dilution (19) was 4486 U/mL, whereas the activity of the purified enzyme (18) was 4170 U/mL, notwithstanding that, due to dilution, the purified formulation (18) contained only about 10 mL of raw amylase per 100 mL of solution. Thus, the activity of the purified enzyme (18), expressed per mL of raw amylase, would be about 41700 U/mL, or about 9.3 times the activity of the original amylase formulation (19).

EXAMPLE 3

Purification of Glucoamylase 5 mL of glucoamylase (Genencor) was blended with 45 mL of 0.05M citrate buffer (pH 4.0), added to 2 g of activated carbon and mixed for 12 h at 250 rpm. The purified enzyme was separated from the activated carbon by filtration. Assays of the raw enzyme solution before dilution (19) and the purified enzyme solution (18) were conducted. The activity of the raw enzyme solution was 980 U/mL, and the activity of the purified enzyme solution was 350 U/mL, notwithstanding that, due to dilution, the purified formulation (18) contained only about 5 mL of raw amylase per 50 mL of solution. Thus, the activity of the purified enzyme (18), expressed per mL of raw amylase, would be about 3500 U/mL, or about 3.6 times the activity of the original amylase formulation (19).

The aforesaid examples show that purification of these two commercial amylase formulations with activated carbon has led to a clear improvement in activity. As hereinbefore mentioned, this improvement in activity may be due to removal of inhibitors from the enzyme solution, or may be due to removal of dispersed solids, e.g., cell debris that may adsorb onto the enzyme and restrict access of substrates to the enzyme active site. The results show that notwithstanding the significant dilution of the commercial formulations, the purified enzyme solutions according to the present invention possess nearly the same activity as the raw commercial enzyme formulations.

Figure 2:
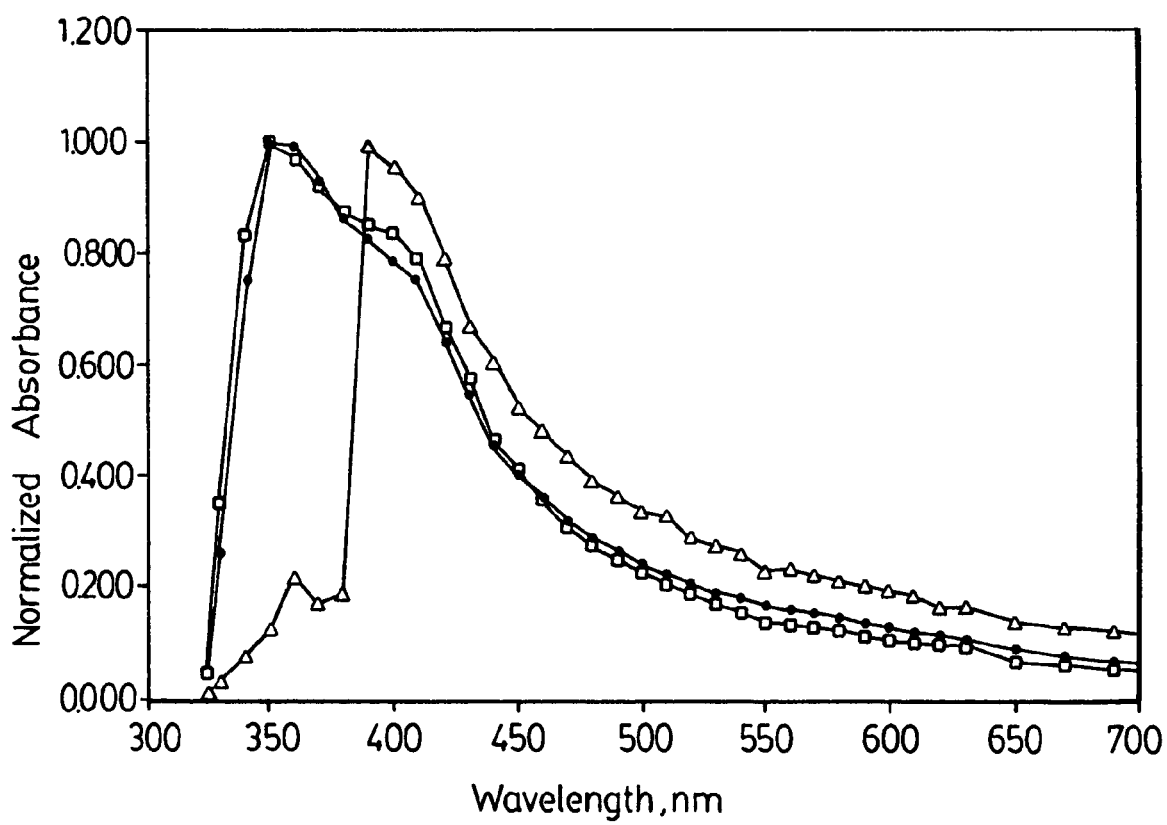
FIG. 2 represents spectral scans of each of (a) raw enzyme, (b) diluted raw enzyme; and (c) purified enzyme.
Figure 3:
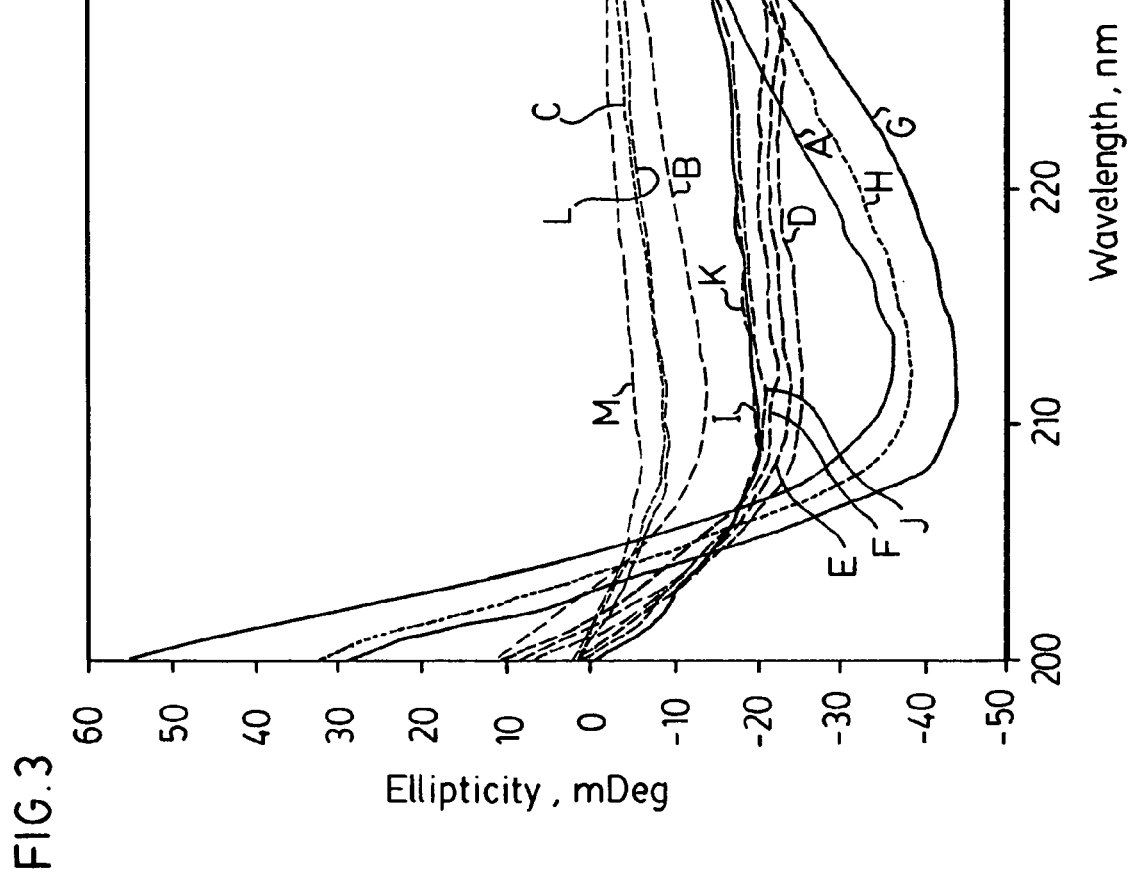
FIG. 3 represents Far UV circular dichroism (CD) spectral scans of each of (a) raw enzyme, and (b) purified enzyme for various commercial amylases and a purified amylase according to the invention.

Evidence that treatment with activated carbon has affected the pre-treated enzyme solution is provided through FIG. 2 and 3, which show spectral scans of the raw, undiluted enzyme (Δ), the modified enzyme (□), and the raw enzyme diluted in water (■). Spectra in FIG. 2 are normalized with respect to their maximum absorbance values, which are 14.5, 1.0, and 1.43 for the raw, purified, and diluted forms, respectively. Clearly, there is a significant spectral shift. Compared to the raw enzyme solution, FIG. 2 illustrates that the purified preparation exhibits enhanced absorbance in the range from 340 to 380 nm, and a reduction in the absorbance from about 390 to 410 nm. The spectrum for the water-diluted preparation is similar to the spectral profile for the purified enzyme preparation, but exhibits a broader peak from 350 to 360 nm and a depression in absorbance from 390 to 440 nm. Similarly, the CD spectra for various enzymes (FIG. 3) show that there is a substantial difference between the purified enzyme (MK10) and other alpha amylases (ALZ, LQZ, SPEZ, and THZ, especially in the range from 205 and 230 nm, as:

_____ALZ_5 A

_____ALZ_6 B

------ALZ_7 C

........LQZ_5 D

.......LQZ_6 E

_____LQZ_7 F

_____MK10_5 G

_____MK10_7 H

_____SPEZ_5 I

_____SPEZ_6 J

-------SPEZ_7 K

.......THZ_6 L

.......THZ_& M

A sensitive aspect of these curves is the differences in wavelength (x axis) as well as differences in ellipticity (y axis). A small shift along the x axis reflects a difference in protein structure. Furthermore, the overall shapes of the curves are indicative of structure. Changes in shape also indicate differences in secondary structure. The CD equipment used for these studies detected wavelength differences as low as 0.1 nm, and thus, a 1 nm shift in the location of the minimum of the spectrum is significant, and a 2 nm shift is most significant.

The MK10 samples (purified amylases) differ from their parents (raw amylases) in that their minima in ellipticity are shifted by at least 2 nm from the minima exhibited by their parents. In one case, the minimum is shifted to the left, and in the other case, it is shifted to the right. However, the 2 nm shift to the left, and in the other case, it is shifted to the right. However, the 2 nm shift is significant, and it represents a significant structural change.

The invention in one preferred form provides a purified enzyme in which the minimum ellipticity on the CD spectrum is shifted by at least 1 nm from its parent (raw) amylase, in the range of between 205 and 230 nm.

Several different shapes of the spectra are also observed. The "dual minima" at ~208 and 222 nm shown by samples D, E, and F are characteristic of an α-helix structure. The purified samples (G and H) do not exhibit such dual minima; rather, they have a fairly sharp minimum that is consistent with a substantially different secondary structure. The process according to the invention leads to changes in secondary structure of the following types:

α-helix→β-sheet

α-helix→uncoiled

β-sheet→α-helix

β-sheet→uncoiled uncoiled→β-sheet

Clearly, some of the other enzyme preparations are also relatively devoid of an α-helix structure, and, thus, although the purified enzymes are not unique in this way, however, a change in secondary structure, e.g. from a structure dominated by α-helices to one devoid of α-helices is significant.

Figure 4:
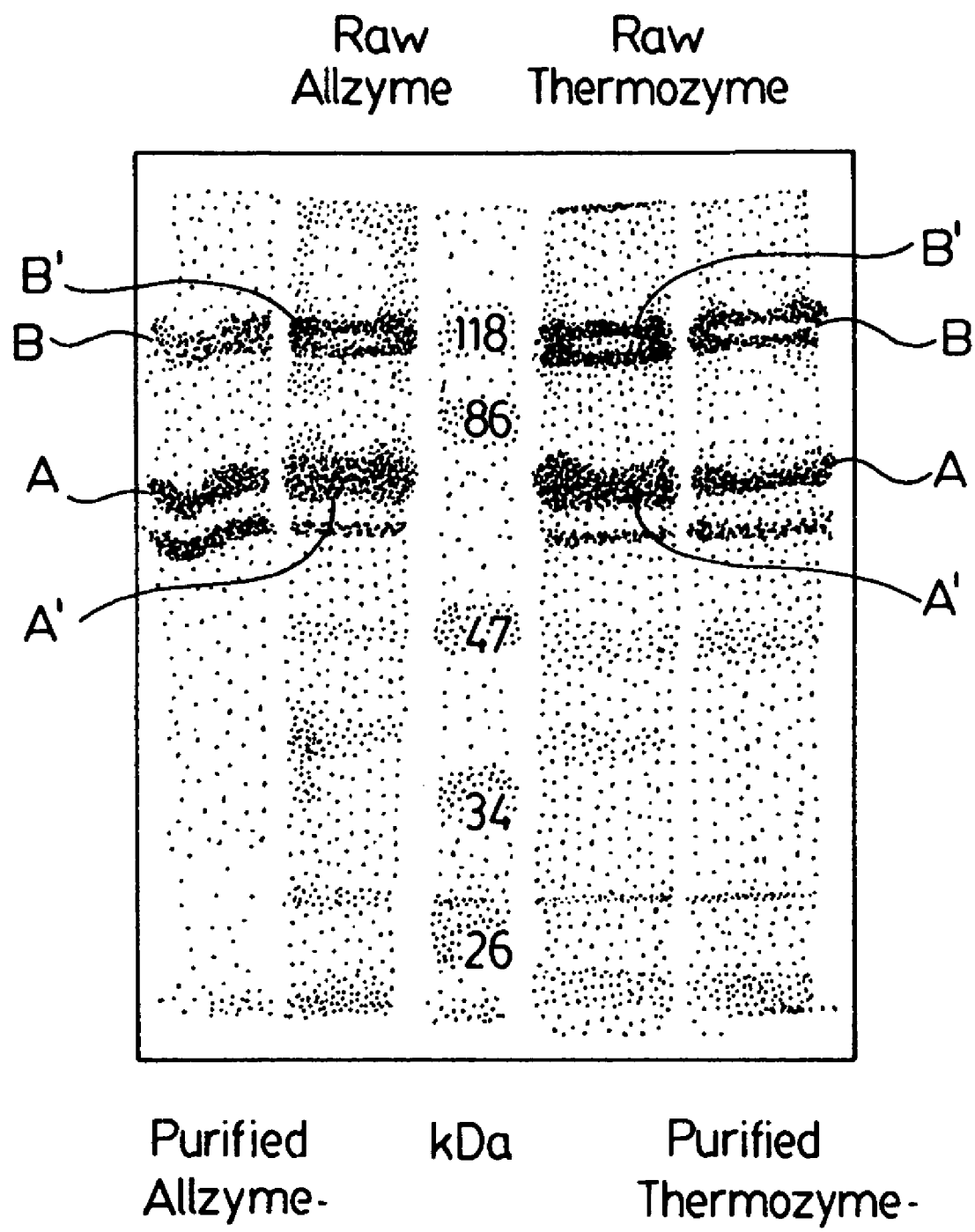
FIG. 4 compares the characteristics of the purified enzyme with those of various commercial raw alpha amylases, as determined by polyacrylamide gel electrophoresis.

When separated by denaturing polyacrylamide electrophoresis (in the presence of sodium dodecyl sulfate and after boiling, i.e., SDS-PAGE), both the native amylases and the purified form exhibit two distinct species between 47 and 86 kDa (FIG. 4). 5 μg of total protein was heat-denatured in the presence of SDS and separated in a 12% Lammeli gel. The image intensity has been log-transformed to clarify the faint lighter species in the source products. The two products differ significantly in the proportion of the two species; namely, raw amylase is more highly populated by the apparently larger species relative to the purified form.

FIG. 4:

Two ratios have been calculated, whereby a first ratio, R, is defined as "top:bottom", and represents the relative quantities of the top and bottom bands. The second ratio is a "recovery ratio", F, defined as "bottom:(top+bottom)". A higher value of F and a lower value of R each indicated a greater proportion of the more active lower band.

The following table summarizes these values:

| Lane | Description | R | F |
|---|---|---|---|
| 1 | Purified Allzyme | 1.6 | 0.39 |
| 2 | Allzyme | 4.7 | 0.18 |
| 3 | Thermozyme | 6.1 | 0.14 |
| 4 | Purified Thermozyme | 2.1 | 0.33 |

Thus, in each case, the process according to the invention has demonstrably increased the proportion of the more active form of the enzyme in the system (comparing purified form 1 vs. raw form 2 and purified form 4 vs. raw form 3).

Figure 5:
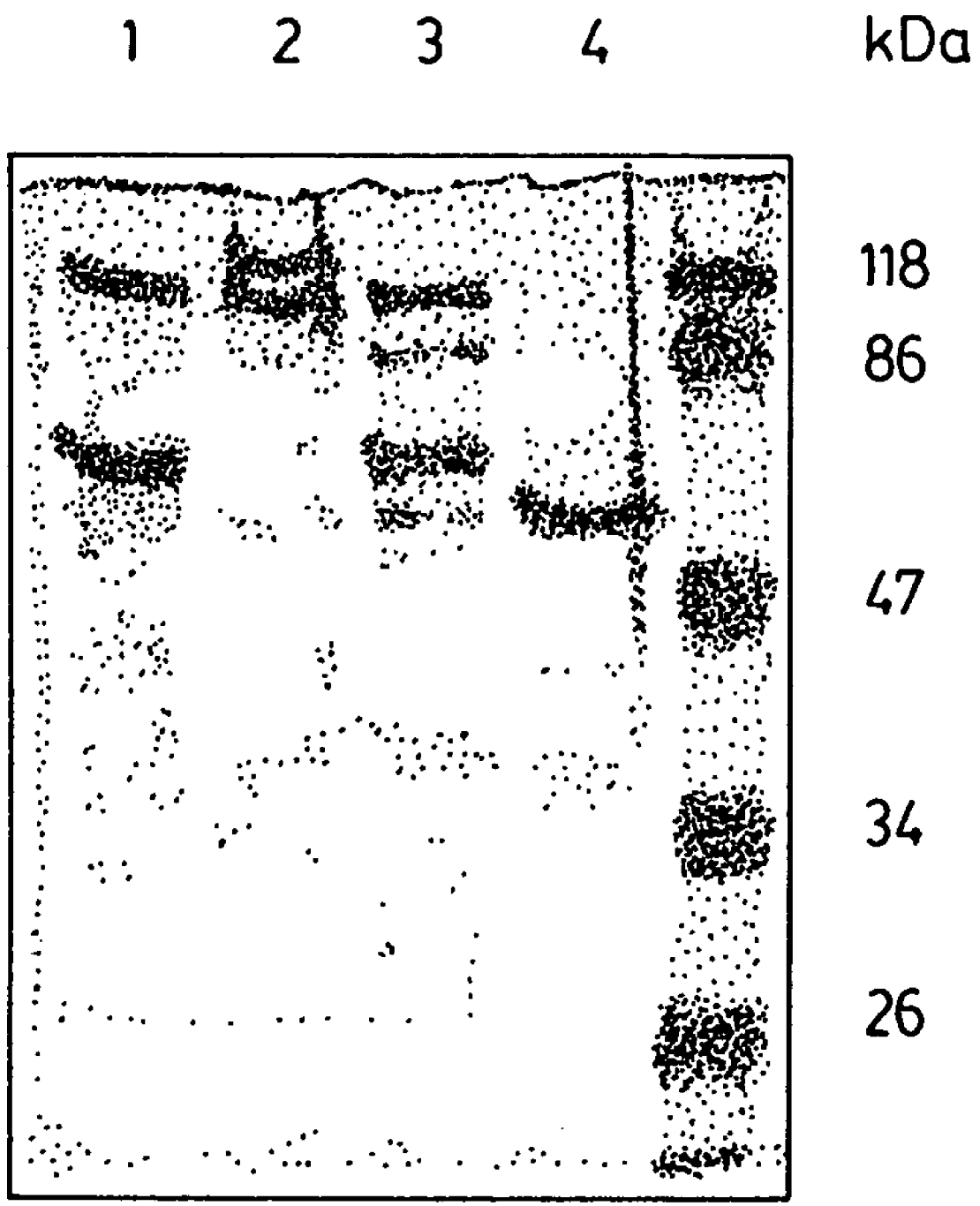
FIG. 5 represents the exhibits heat-sensitive quaternary structure of raw amylase (Allzyme)

Without boiling prior to electrophoresis, the intensity of these two characteristic bands diminish in favour of higher-molecular weight species (above 118 kDa; FIG. 5, lane 2), suggestive of oligomerization. The source enzyme forms SDS-resistant assemblies (Lane 2) which dissociate upon boiling (Lane 1). This structure is not maintained by intermolecular disulfide bonds as the presence of 25% 2-mercaptoethanol exerts no effect (data not shown). Fractions obtained from Sephadex G-100 chromatography performed under native conditions (Lanes 3 and 4) do not appear to interconvert. This proposal is supported by size exclusion chromatography: elution through a Sephadex G-100 column produces two fractions, the first appearing in the void volume (i.e., >100 kDa) and the other in subsequent fractionation volumes. SDS-PAGE analysis of the eluates reveals that the void-volume fraction corresponds to the heavier species on the gel and the other fraction corresponding to the lighter species. The relative amounts of the two fractions track the proportions found in the unfractionated product, i.e., raw amylase, which exhibits a greater fraction of the heavier species in SDS-PAGE, also elutes a larger fraction of its contents in the void volume. Moreover, the two species appear to be stable and do not interconvert even under native conditions (FIG. 5, Lanes 3 and 4).

Figure 6A:
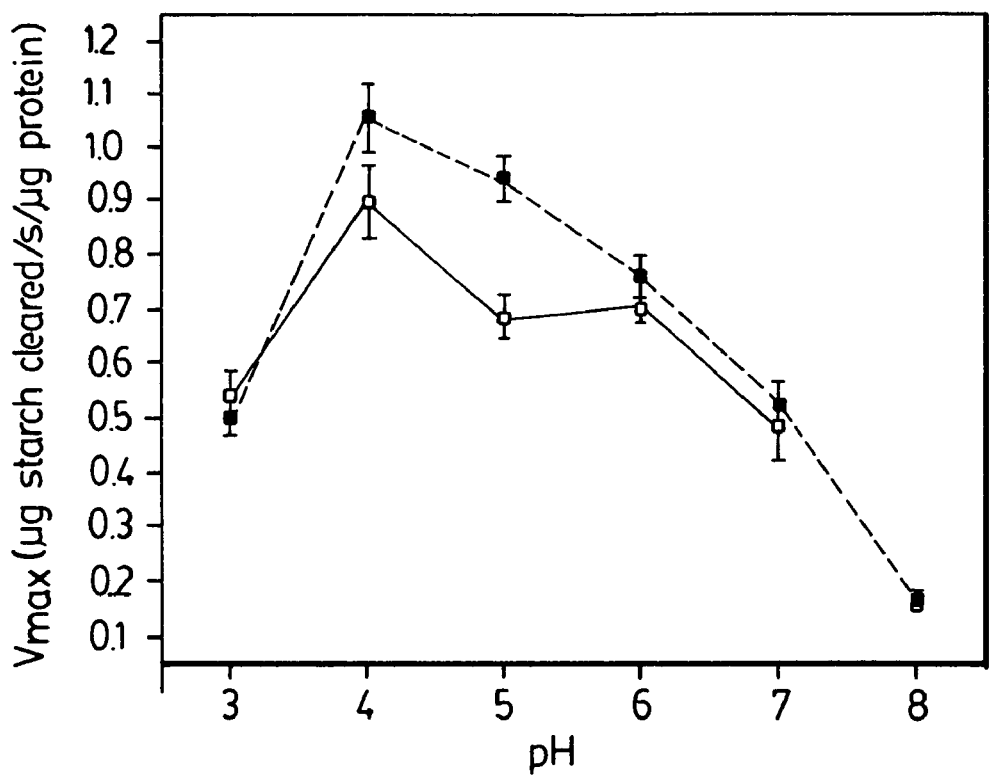
FIG. 6A and FIG. 6B represent the catalytic characteristics of the heavy and light species of raw and purified amylase towards soluble starch, at 25° C. as determined by a standard calorimetric iodine assay.
Figure 6B:
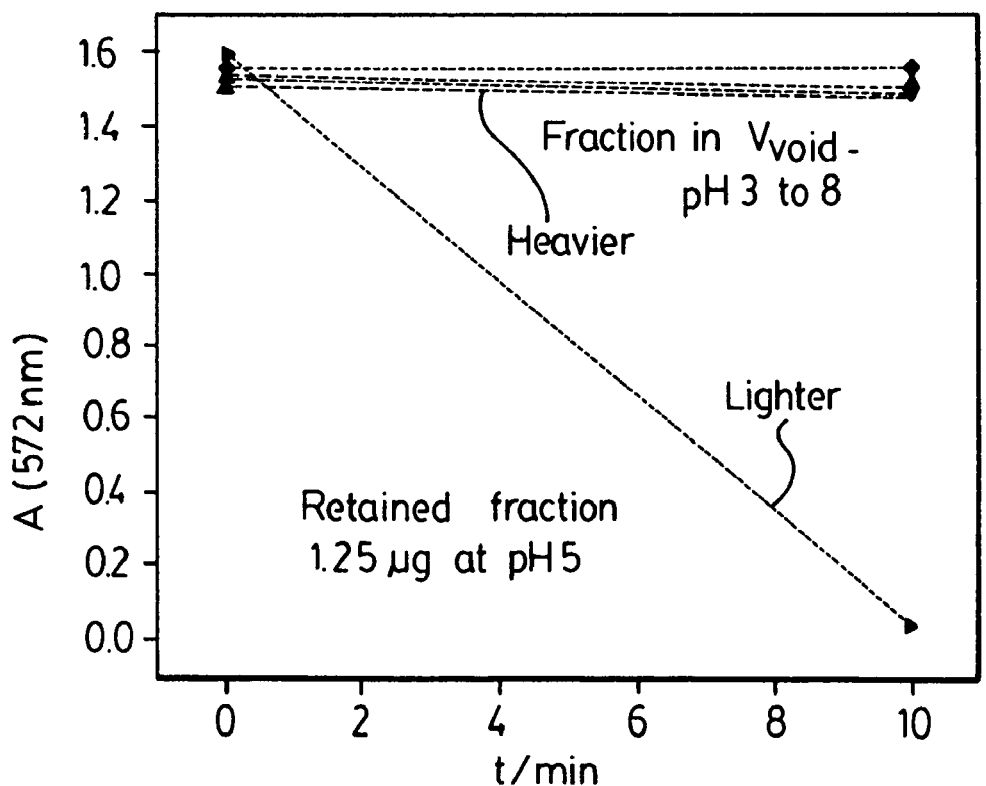

The functional significance of the two species is demonstrated by kinetic assays of their catalytic activities on soluble starch hydrolysis. For raw amylase, the heavier void-volume fraction is catalytically inactive; all of the product's activity resides in the lighter fraction (FIGS. 6A and 6B). A similar observation is found with the purified enzyme. This dichotomy in activity is also indirectly observed in Sephadex chromatography. Kinetics of raw amylase (solid) and purified amylase's light fraction (hollow) from pH 3 to 8. B, 40 μg of heavy species of raw amylase, isolated in the void volume from Sephadex G-100 chromatography, caused no change in starch-iodine staining after 10 min., while 1.3 μg of the lighter species quantitatively cleared iodine staining in the same period at pH 5.

Comparison of the lighter fractions from the two products indicates that they share similar, but not identical, activities, in terms of affinity and turnover, towards soluble starch across a pH range of 3 to 8 at 25° C.; specifically, both display maximal turnover between pH 4 to 5.

In the aggregate, the greater per-unit mass activity found in the purified enzyme can be largely accounted for by a greater proportion of active enzyme and suggest that a significant fraction of enzyme in raw amylase is inactive. The purification/derivatization of raw amylase may result in the conversion of this reservoir of stable, inactive amylase to a catalytically active form.

Although this disclosure has described and illustrated certain preferred embodiments of the invention, it is to be understood that the invention is not restricted to those particular embodiments. Rather, the invention includes all embodiments which are functional or mechanical equivalents of the specific embodiments and features that have been described and illustrated.

The invention claimed is:

1. A method of enhancing the intrinsic enzymatic activity of an enzyme formed from fermentation comprising:
    (a) diluting an enzyme solution comprising glucoamylase with an aqueous solution by a factor of at least three to provide a diluted enzyme solution;
    (b) if the enzyme solution contains cells, filtering the diluted enzyme solution to remove the cells;
    (c) treating the diluted enzyme solution with activated carbon at an effective raw enzyme weight to activated carbon weight ratio of not greater than 25:1 and for a sufficient period of time to effect said enhancement; and
    (d) removing the activated carbon to provide an enzyme solution of enhanced activity.

2. The method according to claim 1, wherein the weight ratio of enzyme to activated carbon is not greater than 15:1.

3. The method according to claim 1, wherein the enzyme activity of the diluted enzyme solution after treatment with activated carbon is at least statistically equivalent to the enzyme activity of the enzyme solution before dilution.

4. The method according to claim 1, wherein the activity of the enzyme solution is enhanced by at least 200%.

5. The method according to claim 1, wherein the enzyme solution is diluted with the aqueous solution by a factor of about 5:1 to 10:1 times.

6. The method according to claim 1, wherein the aqueous solution comprises an aqueous buffer.

7. The method according to claim 1, wherein the aqueous solution comprises water.

8. A method as defined in claim 1 wherein said aqueous solution comprises an aqueous buffer solution.

9. A method as defined in claim 1 wherein said aqueous solution comprises water.

10. A method as defined in claim 1 comprising passing said raw enzyme solution through a column containing an effective amount of said activated carbon.

11. A method as defined in claim 1 wherein said activated carbon is removed by a method selected from the group consisting of filtration and centrifugation.

12. A method as defined in claim 1 wherein said raw enzyme solution is diluted with water to provide a diluted raw enzyme solution.

13. A method as defined in claim 1 wherein said raw enzyme solution is diluted with an aqueous buffer solution to provide a buffered diluted raw enzyme solution.

14. A method as defined in claim 1 wherein said enzyme solution of enhanced activity has a spectrum selected from Far UV (CD) and UV visible spectra distinct from said raw enzyme solution.

15. A method as defined in claim 14 wherein said enzyme solution of enhanced activity shows a relative absorbance intensity lower than said raw enzyme solution, in the CD spectral range of 205-230 nm.

16. A method as defined in claim 14 wherein said enzyme is alpha-amylase and said enzyme solution of enhanced activity has a Far UV (CD) spectrum minimum ellipticity shifted by at least 1 nm, from the raw enzyme solution, in the range between 205-230 nm.

17. A method as defined in claim 1 wherein said enzyme solution of enhanced activity has a UV-visible spectrum maximum peak at least 30 nm lower than said raw enzyme solution.

18. An enzyme solution having enhanced activity made by a method comprising:
    (a) diluting an enzyme solution comprising at least one of glucoamylase or amylase with an aqueous solution by a factor of at least three to provide a diluted enzyme solution;
    (b) if the enzyme solution contains cells, filtering the diluted enzyme solution to remove the cells;
    (c) treating the diluted enzyme solution with activated carbon at an effective raw enzyme weight to activated carbon weight ratio of not greater than 25:1 and for a sufficient period of time to effect said enhancement; and (d) removing the activated carbon to provide an enzyme solution of enhanced activity.

19. The enzyme solution according to claim 18, wherein the enzyme is amylase.

20. The enzyme solution according to claim 18, wherein the enzyme is glucoamylase.

21. The enzyme solution according to claim 18, wherein the activity of the enzyme solution has been enhanced by at least 200%.

22. The method according to claim 18, wherein a pH of the enzyme solution having enhanced activity is from 3 to 8.

23. A method of enhancing the intrinsic enzymatic activity of an enzyme formed from fermentation comprising:
   (a) diluting an enzyme solution comprising amylase with an aqueous solution by a factor of at least three to provide a diluted enzyme solution;
   (b) if the enzyme solution contains cells, filtering the diluted enzyme solution to remove the cells;
   (c) treating the diluted enzyme solution with activated carbon at an effective raw enzyme weight to activated carbon weight ratio of not greater than 25:1 and for a sufficient period of time to effect said enhancement; and
   (d) removing the activated carbon to provide an enzyme solution of enhanced activity.

24. A method as defined in claim 23 wherein said aqueous solution comprises an aqueous buffer solution.

25. A method as defined in claim 23 wherein said aqueous solution comprises water.

26. A method as defined in claim 23 comprising passing said raw enzyme solution through a column containing an effective amount of said activated carbon.

27. A method as defined in claim 23 wherein said activated carbon is removed by a method selected from the group consisting of filtration and centrifugation.

28. A method as defined in claim 23 wherein said raw enzyme solution is diluted with water to provide a diluted raw enzyme solution.

29. A method as defined in claim 23 wherein said raw enzyme solution is diluted with an aqueous buffer solution to provide a buffered diluted raw enzyme solution.

30. A method as claimed in claim 23 wherein said ratio is not greater than 15.

31. A method as defined in claim 23 wherein said enzyme solution of enhanced activity has a spectrum selected from Far UV (CD) and UV visible spectra distinct from said raw enzyme solution.

32. A method as defined in claim 31 wherein said enzyme solution of enhanced activity shows a relative absorbance intensity lower than said raw enzyme solution, in the CD spectral range of 205-230 nm.

33. A method as defined in claim 31 wherein said enzyme is alpha-amylase and said enzyme solution of enhanced activity has a Far UV (CD) spectrum minimum ellipticity shifted by at least 1 nm, from the raw enzyme solution, in the range between 205-230 nm.

34. A method as defined in claim 23 wherein said enzyme solution of enhanced activity has a UV-visible spectrum maximum peak at least 30 nm lower than said raw enzyme solution.

35. A method as defined in claim 23 wherein said enzyme is alpha-amylase and said enzyme solution of enhanced activity has a maximum spectral absorption peak over the range 340 to 360 nm.

36. The method according to claim 23, wherein the weight ratio of enzyme to activated carbon is not greater than 15:1.

37. The method according to claim 23, wherein the enzyme activity of the diluted enzyme solution after treatment with activated carbon is at least statistically equivalent to the enzyme activity of the enzyme solution before dilution.

38. The method according to claim 23, wherein the activity of the enzyme solution is enhanced by at least 200%.

39. The method according to claim 23, wherein the enzyme solution is diluted with the aqueous solution by a factor of about 5:1 to 10:1 times.

40. The method according to claim 23, wherein the aqueous solution comprises an aqueous buffer.

* * * * *